(12) United States Patent
Verbeek et al.

(10) Patent No.: US 6,719,739 B2
(45) Date of Patent: Apr. 13, 2004

(54) SYSTEM AND METHOD FOR ATTACHING UPPER AND LOWER OUTER CASES IN AN IMPLANTABLE DRUG PUMP

(75) Inventors: Maurice T. Y. Verbeek, Geleen (NL); Frans Philippens, Beek (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/940,344

(22) Filed: Aug. 27, 2001

(65) Prior Publication Data

US 2002/0072721 A1 Jun. 13, 2002

Related U.S. Application Data

(60) Provisional application No. 60/229,067, filed on Aug. 30, 2000.

(51) Int. Cl.[7] .............................................. A61M 31/00
(52) U.S. Cl. ............... 604/288.04; 604/500; 604/891.1; 29/428
(58) Field of Search ................................ 604/131, 132, 604/140, 146, 151, 207, 890.1–892.1, 500, 48, 93.01, 288.01–288.04; 264/248, 345–346; 29/428–429

(56) References Cited

U.S. PATENT DOCUMENTS

| | | |
|---|---|---|
| 3,527,220 A | 9/1970 | Summers |
| 3,951,147 A | 4/1976 | Tucker et al. |
| 4,146,029 A | 3/1979 | Ellinwood, Jr. |
| 4,258,711 A | 3/1981 | Tucker et al. |
| 4,714,462 A | 12/1987 | DiDomenico |
| 4,838,887 A | 6/1989 | Idriss |
| 4,931,050 A | 6/1990 | Idriss |
| 4,978,338 A | * 12/1990 | Melsky et al. ............... 604/132 |
| 5,176,641 A | 1/1993 | Idriss |
| 5,443,450 A | 8/1995 | Kratoska et al. |
| 5,575,770 A | 11/1996 | Melsky et al. |
| 5,766,150 A | * 6/1998 | Langkau ..................... 604/140 |
| 5,769,823 A | 6/1998 | Otto |
| 5,814,019 A | * 9/1998 | Steinbach et al. .......... 604/131 |
| 5,836,915 A | 11/1998 | Steinbach et al. |
| 5,837,276 A | 11/1998 | Cheikh |
| 5,908,414 A | 6/1999 | Otto et al. |
| 5,957,890 A | 9/1999 | Mann et al. |

FOREIGN PATENT DOCUMENTS

EP      0 951 916 A2    10/1999

\* cited by examiner

*Primary Examiner*—LoAn H. Thanh
(74) *Attorney, Agent, or Firm*—Stephen W. Bauer; Thomas G. Berry; Curtis D. Kinghorn

(57) ABSTRACT

An implantable pump having a bulkhead, a reservoir structure attached to the bulkhead and upper and lower cases attached to the bulkhead by a single outer seal as well as a method of making such a pump is disclosed. The reservoir structure forms a reservoir that contains fluid drug or other medicaments. The upper and lower cases are attached to the bulkhead by first connecting either the upper or lower case directly to the bulkhead. Then, the lower or upper case not attached to the bulkhead is attached to the upper or lower case that had been previously attached to the bulkhead.

14 Claims, 13 Drawing Sheets

SYSTEM AND METHOD FOR ATTACHING UPPER AND LOWER OUTER CASES IN AN IMPLANTABLE DRUG PUMP

RELATED APPLICATIONS

This application claims the benefit of provisional application, U.S. Ser. No. 60/229,067, filed Aug. 30, 2000, entitled "SYSTEM AND METHOD FOR ATTACHING UPPER AND LOWER OUTER CASES IN AN IMPLANTABLE DRUG PUMP", by Maurice T. Y. Verbeek and Frans Philippens.

BACKGROUND OF THE INVENTION

1. Field of the Invention

The present invention relates to implantable medication delivery devices that are implanted within the body of a patient to deliver drugs or other fluid medicaments and methods of construction of the devices. More particularly, the invention relates to techniques for sealingly attaching upper and lower outer cases to a bulkhead in such medication delivery devices.

2. Description of the Related Art

When chronic administration of a pharmaceutically active agent is required, an implantable infusion pump ("IIP") 10, having a reservoir 12 connected to a catheter 14, may be the desired delivery means (FIG. 1). For example, a IIP-catheter delivery system may be preferred when it is important to deliver the agent to a specific site or when the agent must be administered to spaced sites in tightly controlled, yet minute dosages.

Catheter 14 is connected to IIP 10 and carries fluid medicament from the reservoir 12 in IIP 10 to a desired location in a body. The IIP 10 and catheter 14 are implanted within the body.

A number of approaches have been followed in the prior art for the dispensing of medical substances in the body. One particularly effective method has been to implant a reservoir of fluid medical substances and a pump in a patient's body. The reservoir and pump are connected to a catheter that delivers the fluid medical substance to a desired location in the body.

A number of reservoirs, pumps and combinations of reservoirs and pumps have been developed. For example, U.S. Pat. No. 3,527,220 shows an implantable drug administrator that operates with a refillable bladder reservoir and a roller pump that is driven by a magnet located outside the body. U.S. Pat. No. 3,951,147 shows a reservoir formed from a bellows enclosed within a housing. The contents of the reservoir are pressurized by a fluorocarbon fluid located in the space between the housing and bellows. The unit continuously dispenses the liquid to the body site through a capillary tube. U.S. Pat. No. 4,146,029 shows a dispenser that dispenses drugs in a predetermined manner which may be modified somewhat by means external to the body. A piston and bellows pumping device is used to dispense the drug.

Additional pumps and reservoirs are shown in U.S. Pat. No. 4,931,050, issued Jun. 5, 1990 to Samir F. Idriss entitled "Constant Pressure Variable Flow Pump"; U.S. Pat. No. 4,838,887, issued Jun. 5, 1990 to Samir F. Idriss entitled "Programmable Valve Pump"; U.S. Pat. No. 4,714,462, issued Jun. 5, 1990 to Robert A. DiDomenico entitled "Positive Pressure Programmable Infusion Pump"; U.S. Pat. No. 4,714,462, issued Jun. 5, 1990 to Samir F. Idriss entitled "Passive Shuttle Metering Device For Implantable Drug Delivery System"; and U.S. Pat. No. 5,176,641 issued Jan. 5, 1993 to Samir F. Idriss entitled "Implantable Drug Infusion Reservoir Having Fluid Impelling Resilient Foam Member".

Further pumps and reservoirs are shown in U.S. Pat. No. 5,575,770 issued Nov. 19, 1996 to Gerald S. Melsky and Bradley J. Enegren entitled "Implantable Drug Infusion System With Safe Bolus Capability"; U.S. Pat. No. 4,978,338 issued Dec. 18, 1990 to Gerald S. Melsky and Frank R. Prosl entitled "Implantable Infusion Apparatus"; U.S. Pat. No. 5,908,414 issued Jun. 1, 1999 to Karl-Heinz Otto, Manfred Wieland, Hans Baumann and Jorg-Roger Peters entitled "Implantable Infusion Pump"; and U.S. Pat. No. 5,769,823 issued Jun. 23, 1998 to Karl-Heinz Otto entitled "Implantable Infusion Pump". The collective teachings of the patents listed above are incorporated herein in their entireties by reference.

A typical IIP 10 for storing and delivering fluid medicaments to a desired location in a body according to the present invention is shown in cross-section in FIGS. 2 and 3. As mentioned above, IIP 10 stores and dispenses medical substances from a reservoir 12. Reservoir 12 is formed by a reservoir structure 16 having a reservoir structure upper end 18 and a reservoir structure terminal end 20. Reservoir structure 16 is typically a bellows 22 having pleated sides 24 and a substantially planar bottom 26 sealingly connected to the sides 24. Pleated sides 24 are made up of a series of inwardly directed annular rings 28 and outwardly directed annular rings 30 sealingly connected at inner connection points 32 and outer connection points 34. In the typical IIP 10, bellows 22 terminates at its upper end 18 with an ultimate inwardly direct annular ring 36. Ultimate inwardly direct annular ring 36 terminates in a bellows terminal end 38 so that the bellows terminal end 38 is the reservoir structure terminal end 20 for a bellows type reservoir structure 16. Bottom 26 is usually circular so that bellows 22 is cylindrical. Because bellows 22 is cylindrical, bellows terminal end 38 is annular.

Bellows terminal end 38 is connected to an annular bracket 40. Viewed in cross-section, bracket 40 has a horizontal leg 42. Horizontal leg 42 has an inner terminal end 43 and an outer terminal end 44. Bellows terminal end 38 is connected to bracket 40 at 45 near the inner terminal end 43 by means well understood in the art such as welding. Annular bracket 40 also includes a vertical leg 46. Vertical leg 46 has an upper terminal end 47 and a lower terminal end 48.

IIP 10 also includes a bulkhead 50 having a top surface 52, a bottom surface 54 and an outer periphery 56. IIP 10 includes a metering system 58 usually attached to the top surface 52 of bulkhead 50. Metering system 58 may take the form of a peristaltic pump, a piston pump, a tubular or micro-machined capillary flow restrictor, a piezoelectric micropump or other metering means as will clear to those skilled in the art. Metering system 58 is connected to reservoir 12 through an output conduit 60.

The bottom surface 54 of bulkhead 50 includes an annular recess 62 extending into bulkhead 50 toward top surface 52. Recess 62 has an inner vertical wall 64 and a horizontal wall 65 connected together at 66. Recess 62 also has an outer vertical wall 67 connected to the horizontal wall 65 at 68. Horizontal leg 42 is about the same length as horizontal wall 66 while vertical leg 46 is about the same length as outer vertical wall 67. Bellows 22 is attached to bulkhead 50 at recess 62 by bracket 40 as described below.

IIP 10 also typically has a primary self-sealing septum 70 through which a drug, fluid or other medicament is placed in the reservoir 12. A hypodermic needle can be inserted through the skin and through the primary seal-sealing septum 70 into a chamber 72 that is connected to reservoir 12 through an inlet conduit 74. Through the hypodermic needle, a quantity of a liquid agent, such as a medication, a growth factor, an antisense agent, an ionic solution, one or more antibodies, a hormone, proteins or peptides, viruses, cell suspension, a chemotherapeutic agent or toxin or some drug is inserted into the reservoir 12. The liquid agent is then delivered from reservoir 12 through the metering system 58 and through catheter 14 that is attached to IIP 10 through a catheter connector 76 that is attached to the metering system 58. The catheter 14 is positioned to deliver the agent to infusion sites in the patient's body.

IIP 10 may also have a catheter access port septum 78 through which a bolus injection of drug, fluid or other medicament may be administered directly to the patient through the catheter 14, bypassing the metering system 58. Catheter access port septum 78 may also be used to take a sample of cerebrospinal fluid (CSF) from catheter 14 or for checking the patency of catheter 14 in the event of a loss of therapeutic benefit.

As shown in detail in FIG. 4, IIP 10 also includes an upper case 80 and a lower case 82 that substantially defines the outer dimensions of IIP 10 and protects the inner parts, bellows 22, bulkhead 50 and metering system 58, of IIP 10. Upper case 80 has a substantially flat upper surface 84 and a substantially cylindrical side wall 86. Side wall 86 terminates in a terminal end 88. Because side wall 86 is typically cylindrical, terminal end 88 is circular.

Lower case 82 has a substantially flat bottom surface 90 and a substantially cylindrical side wall 92. Side wall 92 terminates in a terminal end 94. Because side wall 92 is typically cylindrical, terminal end 94 is circular.

Upper and lower cases 80, 82 are typically attached to the bulkhead 50 at the outer periphery 56 of the bulkhead 50. This is accomplished by attaching upper and lower cases 80, 82 to a protrusion 96 that extends away from the outer periphery 56. Protrusion 96 has an upper surface 98 and a lower surface 100. The width of upper surface 98 is the same as the thickness of the material of side wall 86. Likewise, the width of lower surface 100 is the same as the thickness of the material of side wall 92.

Upper case 80 is brought into contact with protrusion 96 so that terminal end 88 is brought into contact with the upper surface 98 of protrusion 96. Terminal end 88 is then connected to protrusion 96 by means such as welding at 102 so that a sealed seam is created at 102 between upper case 80 and protrusion 96.

Likewise, lower case 82 is brought into contact with protrusion 96 so that terminal end 94 is brought into contact with the lower surface 100 of protrusion 96. Terminal end 94 is then connected to protrusion 96 by means such as welding at 104 so that a sealed seam is created at 104 between lower case 82 and protrusion 96.

A propellant chamber 106 is placed between lower case 82 and the reservoir structure 16. A propellant gas is place in propellant chamber 106. The propellant gas acts as a pressure-providing means to the reservoir structure 16 that compresses the reservoir structure 16 to discharge the drug or other agent stored in the reservoir 12. The propellant gas used to drive such a "gas driven" IIP 10 is a fluid that is in phase change between a liquid state and a gas state when, i.e., in equilibrium between phases at around 35–37 degrees (Celsius), which is the usual temperature range of the human body.

In a particular type of IIP 10, metering system 58 takes the form of a tubular or micro-machined capillary flow restrictor. In such a pump, the medical substance is dispensed from the reservoir 12 at a constant rate that depends primarily on the geometry of the tubular or micro-machined flow restrictor. In such a IIP 10, it is relatively important that the pressure in propellant chamber 106 be maintained at a higher pressure than is necessary in a IIP 10 having a metering system 58 comprising a peristaltic pump, a piston pump or a piezoelectric micropump. For example, the propellant pressure in a peristaltic pump such as the Synchromed® pump manufactured and sold by Medtronic, Inc. of Minneapolis, Minn. is about 0.276 bar (4.00 Psi). On the other hand, the propellant pressure in a constant rate pump having a tubular flow restrictor such as the IsoMed® pump also manufactured and sold by Medtronic, Inc. of Minneapolis, Minn. is about 2.10 bar (30.46 Psi). The reason for a higher pressure in the propellant chamber 106 in a constant rate IIP 10 with a capillary tube flow restrictor is that this higher pressure reduces the variability in flow rates of the drug or other agent due to atmospheric conditions such as barometric pressure.

In manufacturing IIP 10, the bellows terminal end 38 of bellows 22 is attached to the horizontal leg 42 of bracket 40 near the inner terminal end 43 by means such as welding. Since both bellows terminal end 38 and bracket 40 are annular, bellows terminal end 38 is connected to bracket 40 around an annular path as connection point 45 is moved around horizontal leg 42. At this stage of the manufacturing process, access to connection point 45 is relatively free since bellows 22 has not yet been joined to bulkhead 50.

Once bellows terminal end 38 has been joined to horizontal leg 42 of bracket 40, bracket 40 is moved onto horizontal wall 66 of recess 62. As described above, horizontal leg 42 is about the same length as horizontal wall 66. This allows bracket 40 to be moved into recess 62 so that the inner terminal end 43 of horizontal leg 42 comes into contact with horizontal wall 66. In this position, vertical leg 46 also comes into contact with outer vertical wall 67. Bracket 40 is then connected to the recess 62 at lower terminal end 48 by means such as welding around the entire annular lower terminal end 48. In this way, bellows 22 is sealingly attached to bulkhead 50 at lower terminal end 48 of bracket 40.

The prior art system of connecting upper and lower cases 80, 82 to bulkhead 50 at protrusion 96 requires two outer seals 102, 104, respectively. Because there are two seals 102, 104, there is twice the likelihood that a defect will be formed in or develop in a seal than would be present in a single seal. It is therefore desirable to attach upper and lower cases 80, 82 to bulkhead 50 with a single outer seal.

SUMMARY OF THE INVENTION

An implantable pump having a bulkhead, a reservoir structure attached to the bulkhead and upper and lower cases attached to the bulkhead by a single outer seal as well as a method of making such a pump is disclosed. The reservoir structure forms a reservoir that contains fluid drug or other medicaments. The upper and lower cases are attached to the bulkhead by first connecting either the upper or lower case directly to the bulkhead. Then, the lower or upper case not attached to the bulkhead is attached to the upper or lower case that had been previously attached to the bulkhead.

It is an object of the invention to create an implantable pump having upper and lower outer cases sealingly attached to form an outer seal.

It is a further object of the invention to make such a pump that is relatively easy to manufacture.

These and other objects of the invention will be clear from the description of the invention contained herein and more particularly from the description in conjunction with the drawings attached hereto. Throughout this description, wherever referred to, like elements are referred to by like reference numbers and have all the described features and characteristics of the element unless specifically stated otherwise. Further, features of certain embodiments may be applicable to combining with other embodiments as will be clear to those skilled in the art.

BRIEF DESCRIPTION OF THE DRAWINGS

The advantages of the present invention will become more apparent by referring to the following detailed description and accompanying drawings, in which.

DESCRIPTION OF THE PREFERRED EMBODIMENTS

Figure 1:
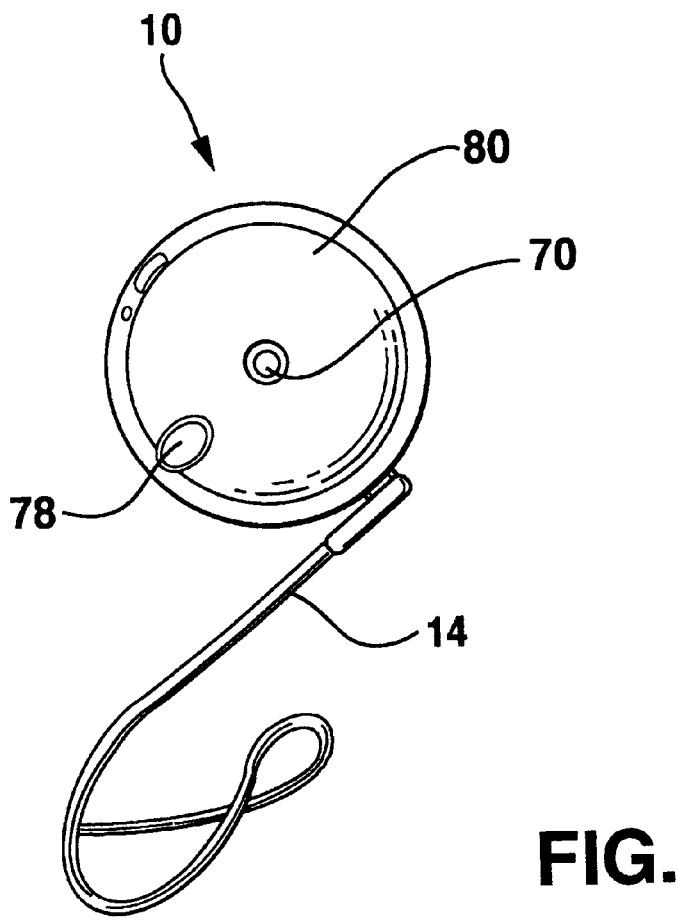
FIG. 1 is a perspective view of a pump and catheter system.
Figure 2:
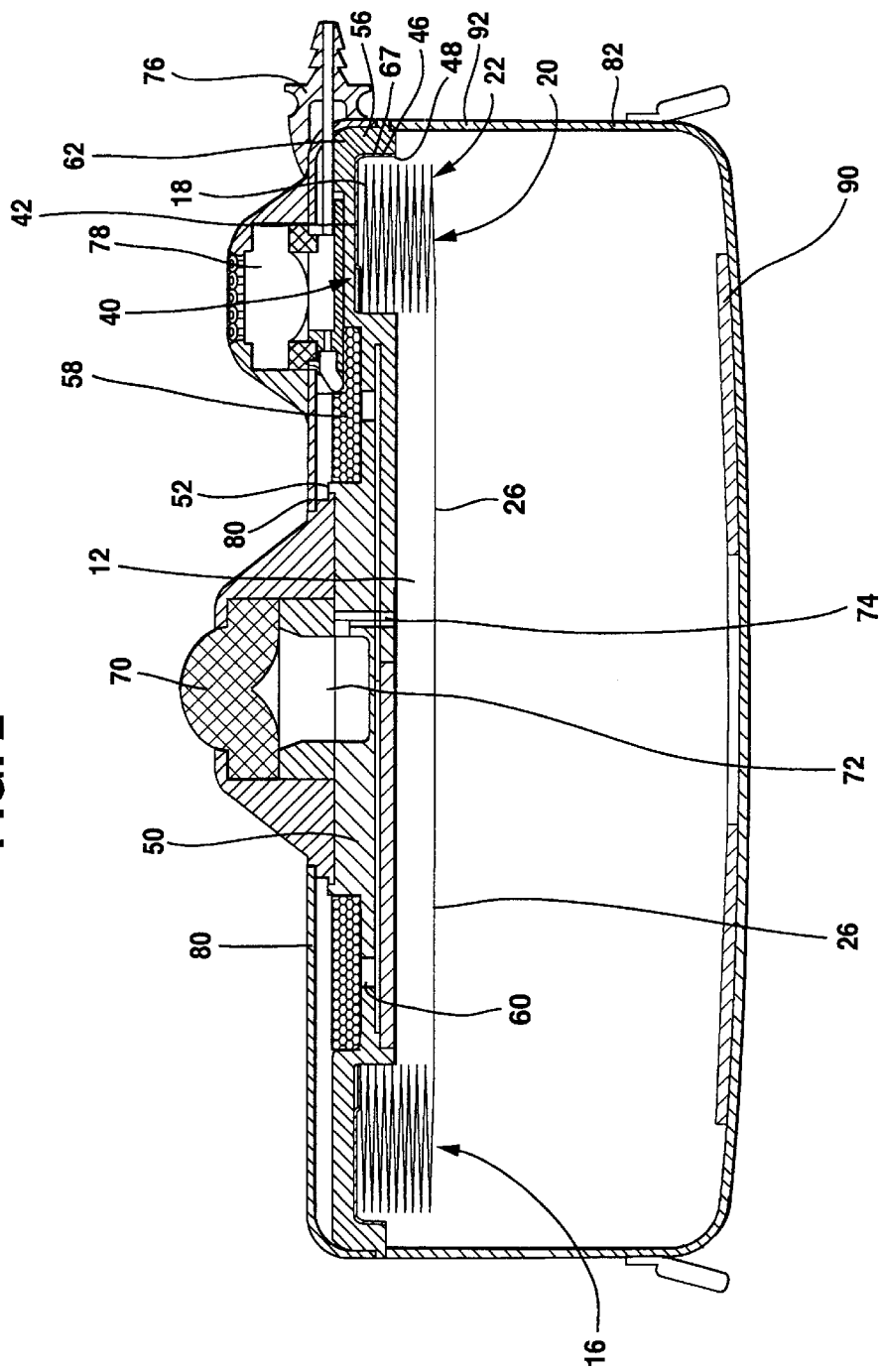
FIG. 2 is a side cross-sectional view of the typical pump of FIG. 1.
Figure 3:
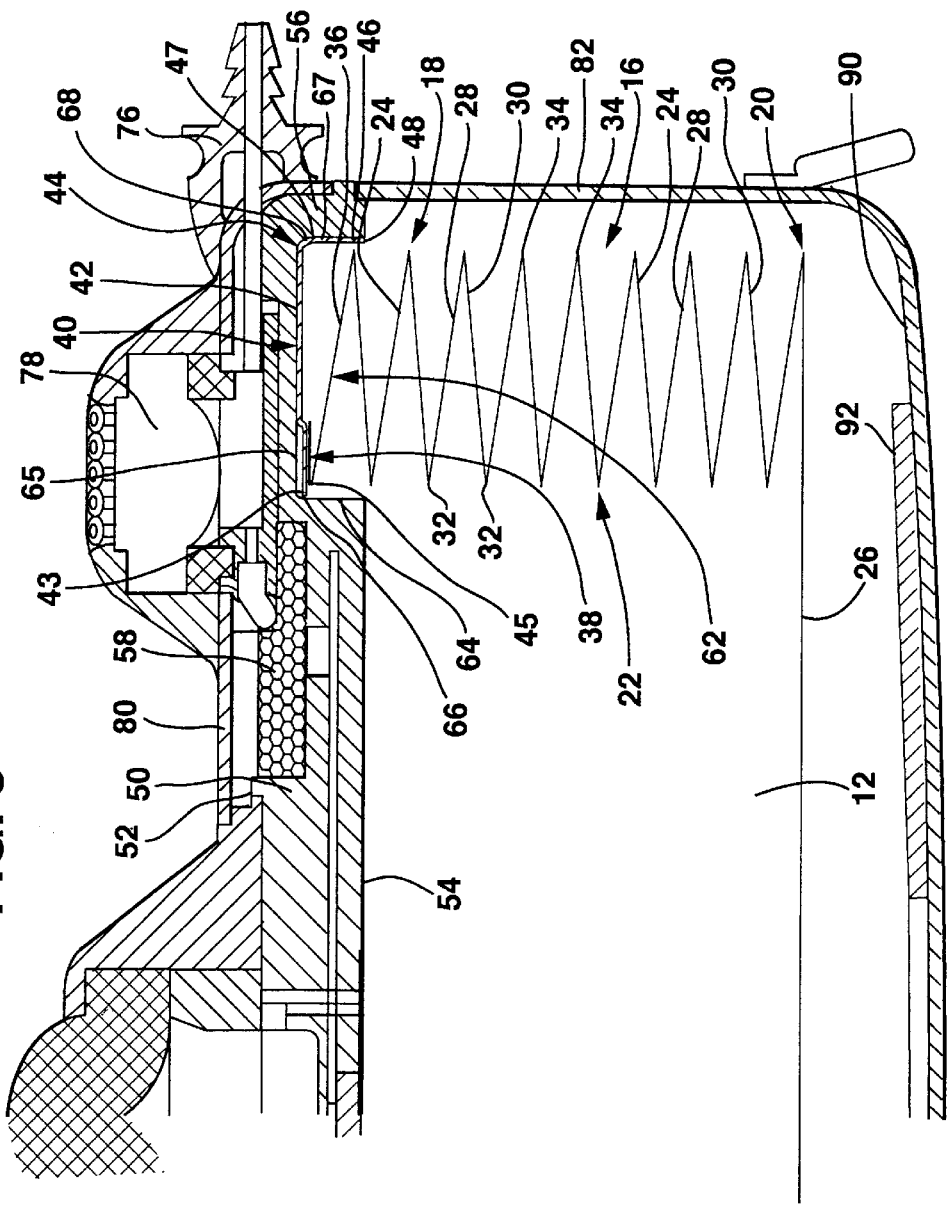
FIG. 3 is a close-up side cross-sectional view of the typical pump of FIG. 1.
Figure 4:
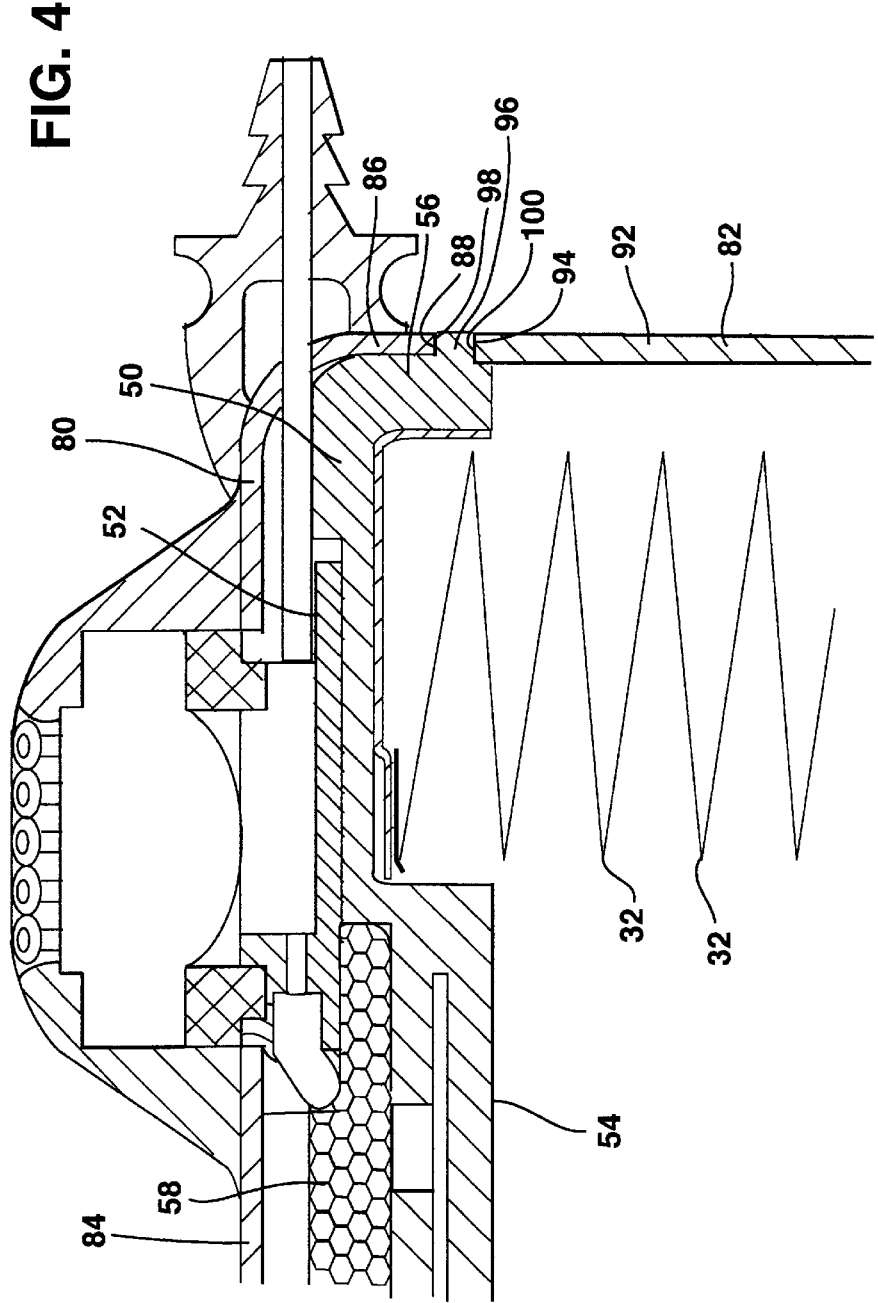
FIG. 4 is a close-up side cross-sectional view of the connection of the upper and lower cases to the bulkhead in the typical pump of FIG. 1.

An IIP 10 according to the present invention is shown in FIGS. 5–13. IIP 10 in the present invention includes a reservoir structure 16, preferably in the form of a bellows 22 and metering system 60 as described above. IIP 10 also includes a bulkhead 50.

FIGS. 5–8 shows a particular embodiment of the invention. In this embodiment, the outer periphery 56 does not have a protrusion 96. Instead, outer periphery 56 has an annular recess 108 that extends around the outer periphery 56 at the lower edge 110 of outer periphery 56. Recess 108 has a recess top 112 that is closer to the top surface 52 of bulkhead 50 than is the lower edge 110. A recess vertical wall 116 connects the recess top 112 to the lower edge 110. Lower edge 110 transitions to recess vertical wall 116 at 118. Recess top 112 has a width about equal to the thickness of lower case 82.

Recess top 112 is preferably not perpendicular to recess vertical wall 116. Instead, recess top 112 is preferably obtuse to recess vertical wall 116 for a purpose to be explained hereafter.

The side wall 92 near the terminal end 94 of the lower case 82 is modified as follows. An inward bend 120 is formed so that the ultimate end 122 of sidewall 92 near terminal end 94 is substantially parallel, although inwardly displaced, to the side wall 92 of lower case 82 opposite inward bend 120. The amount of displacement of the terminal end 94 of lower case 82 is about equal to the thickness of the upper case 80.

Figure 5:
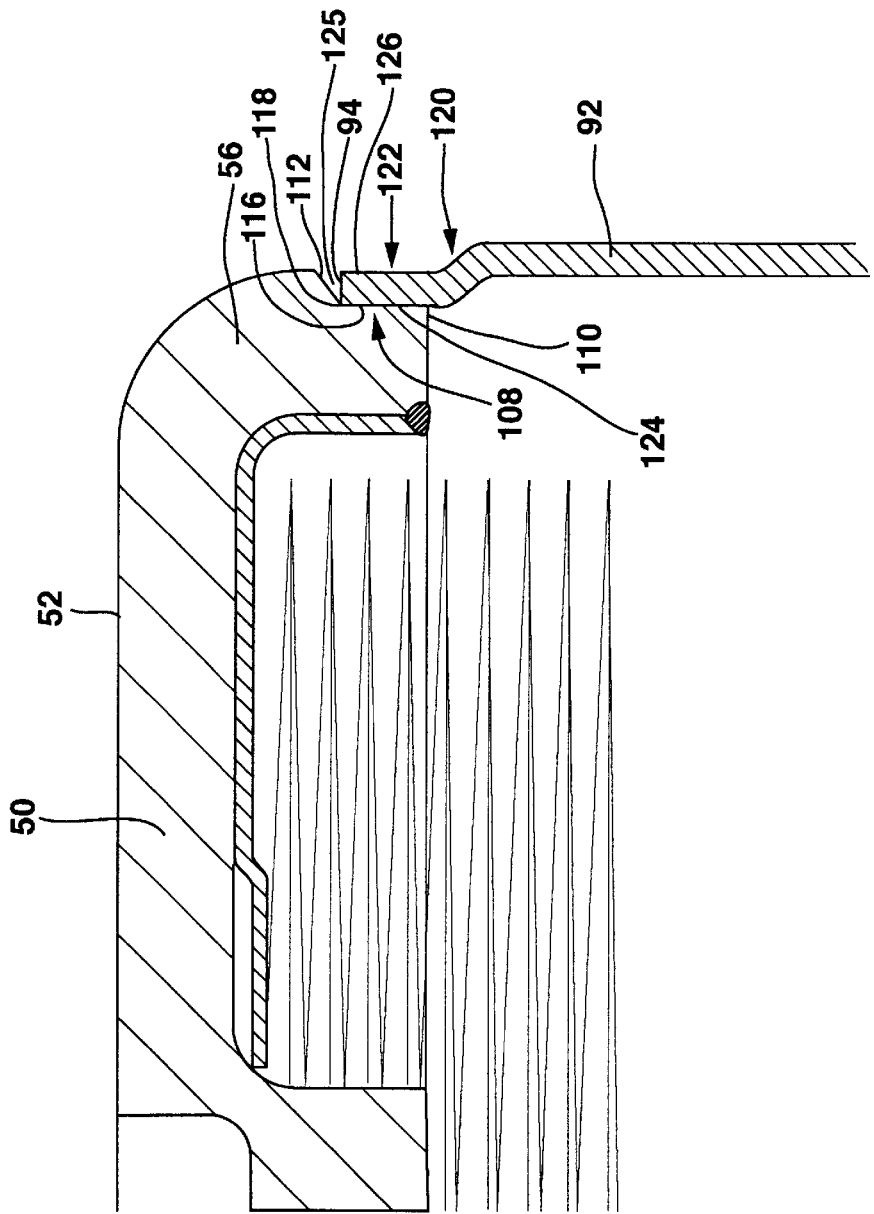
FIG. 5 is a side cross-section view of the placement of the lower case with respect to the bulkhead in one embodiment of the present invention.

To assemble IIP 10, the terminal end 94 of lower case 82 is placed in recess 108 so that the terminal end 94 is located approximately at the recess top 112 (FIG. 5). In this position, the inner surface 124 of side wall 92 near the terminal end 94 is in contact with the recess vertical wall 116. In addition, as described above, because recess top 112 is obtuse to the recess vertical wall 116, the recess top 112 also forms an acute angle with respect to the terminal end 94 of lower case 82. As a result, there is a space 125 between the terminal end 94 and the recess top 112.

Figure 6:
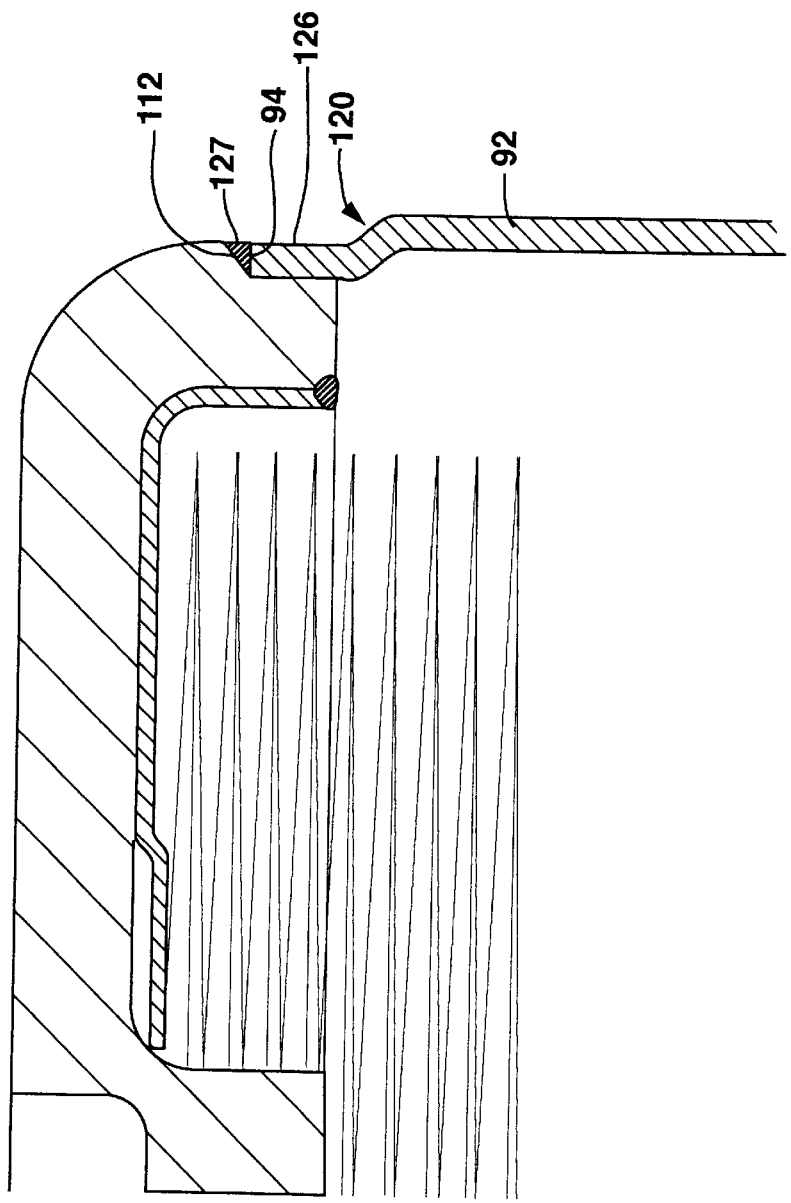
FIG. 6 is a side cross-section view of the connection of the lower case to the bulkhead in the embodiment of FIG. 5.

As described above, the terminal end 94 of lower case 82 is placed in recess 108 to so that the terminal end 94 is located approximately at the recess top 112. Terminal end 94 is attached to bulkhead 50, preferably by welding, so that a weld 127 fills the space 125 between the terminal end 94 and recess top 112 (FIG. 6). Preferably, when space 125 is filled with the weld 127 to connect terminal end 94 to bulkhead 50, the weld 127 should be about co-linear with the outside surface 126 of the terminal end 94 of lower case 82. The weld 127 in space 125 forms a seal between bulkhead 50 and the lower case 82.

Figure 7:
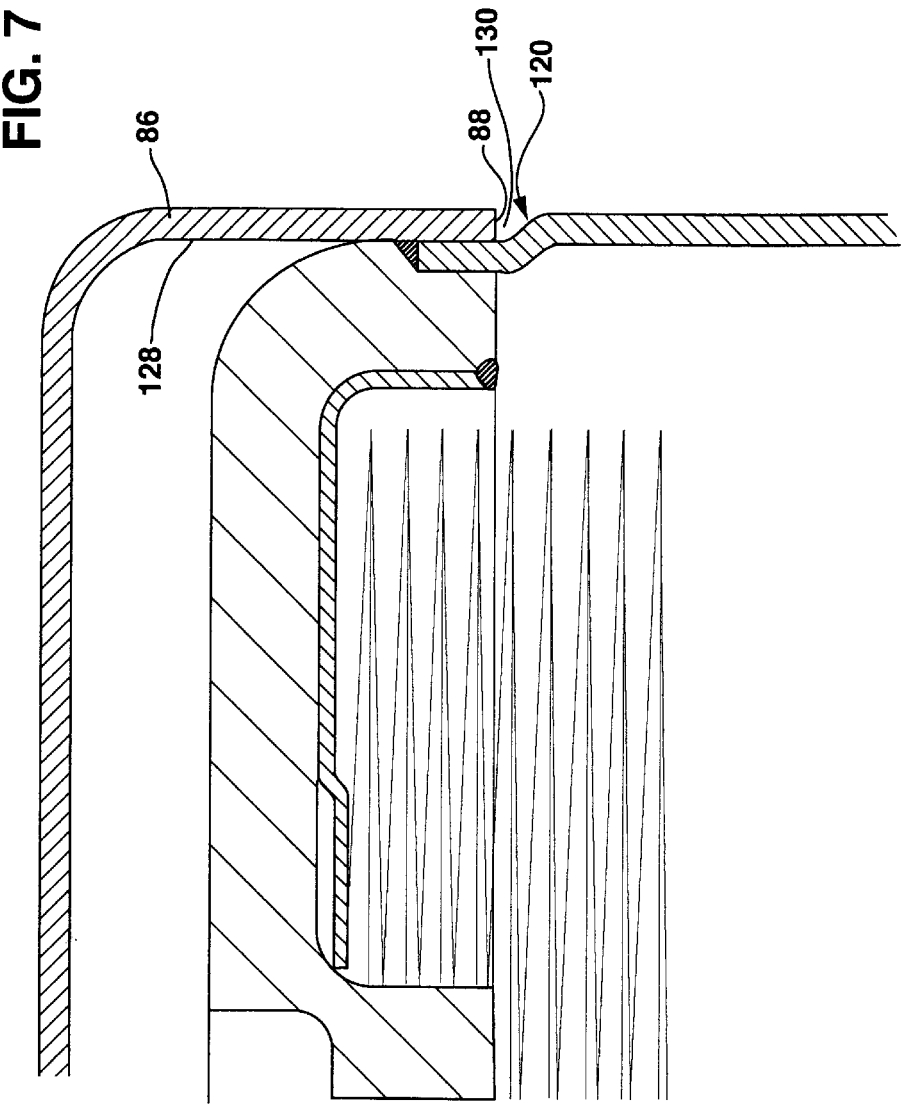
FIG. 7 is a side cross-section view of the placement of the upper case on the lower case in the embodiment of FIG. 5.

After lower case 82 has been attached to bulkhead 50 as described above, the upper case 80 is attached to lower case 82. This is done by moving the terminal end 88 of upper case 80 into contact with the outer surface 126 of the terminal end 94 of lower case 82 so that the inside surface 128 of upper case 80 is in contact with the outside surface 126 of terminal end 94 (FIG. 7). Further, the terminal end 88 is moved to approximately the location of inward bend 120. This produces a space 130 between the terminal end 88 of upper case 80 and the material of lower case 82 near the inward bend 120.

Figure 8:
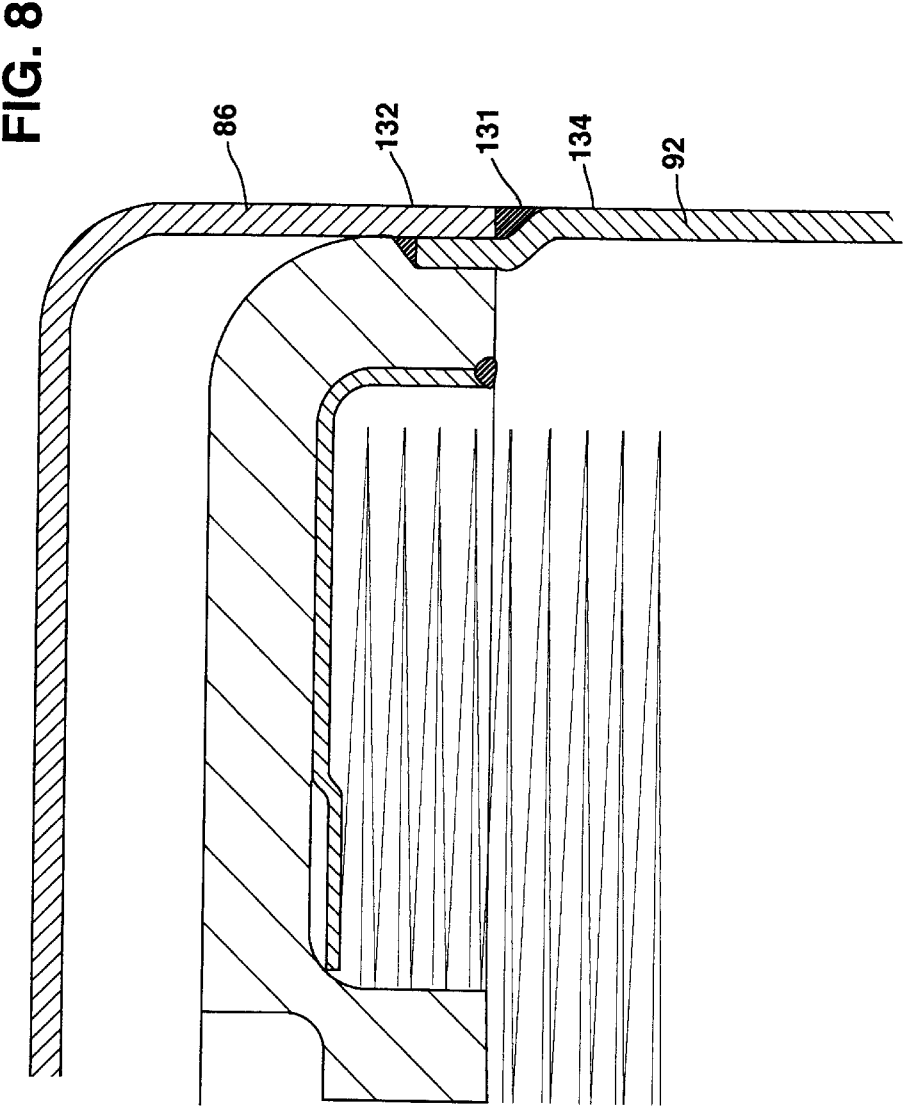
FIG. 8 is a side cross-section view of the connection of the upper case to the lower case in the embodiment of FIG. 5.
Figure 9:
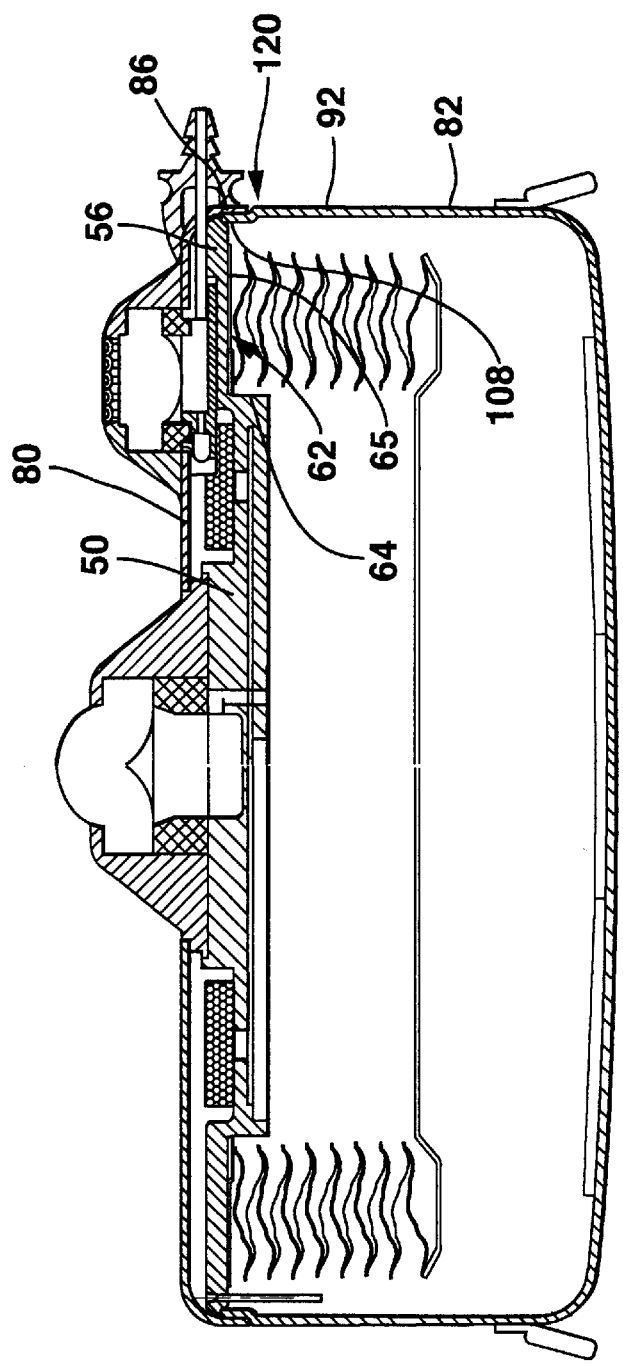
FIG. 9 is a side cross-section view of an alternate embodiment of the present invention.

Upper case 80 is attached to lower case 82, preferably by welding upper case 80 to lower case 82 in space 130 by a weld 131 (FIG. 8). Since space 130 extends entirely around the IIP 10, upper case 80 is attached to lower case 82 by the weld in space 130 entirely around the outer periphery of IIP 10. Also, the weld in space 130 should attach upper case 80 to lower case 82 and thereby entirely fill space 130 but should not extend above the outer surface 132 of upper case 80 and outer surface 134 of lower case 82. As a result, upper case 80 is attached to lower case 82 through a single seal formed by the weld in space 130 instead of the two seals 104, 106 required by the prior art IIP 10.

A variant of the invention described above is shown in FIG. 9. In this embodiment, bulkhead 50 is modified so that the annular recess 62 that extends into bulkhead 50 toward top surface 52 does not have an outer vertical wall 67 connected to the horizontal wall 65 at 68. Instead, horizontal wall 65 extends from the inner vertical wall 64 to the ultimate outer periphery of bulkhead 50.

In this embodiment, recess 108 is shorter than in the embodiment described above. In all other ways, recess 108 and upper and lower cases 80, 82 are as structured and connected as described above.

In another variant of the invention described above, as shown in FIGS. 10–13, upper case 80 is attached to bulkhead 50 and lower case 82 is attached to upper case 80. Again, in this embodiment, the outer periphery 56 does not have a protrusion 96. Instead, outer periphery 56 has an annular recess 136 that extends around the outer periphery 56 at the upper edge 138 of outer periphery 56. Recess 136 has a recess bottom 140 that is closer to the bottom surface 54 of bulkhead 50 than is the upper edge 138. A recess vertical wall 142 connects the recess bottom 140 to the upper edge 138. Upper edge 138 transitions to recess vertical wall 142 at 144. Recess bottom 140 has a width about equal to the thickness of upper case 80.

Recess bottom 140 is preferably not perpendicular to recess vertical wall 142. Instead, recess bottom 140 is preferably obtuse to recess vertical wall 142 for a purpose to be explained hereafter.

The side wall 86 near the terminal end 88 of the upper case 80 is modified as follows. An inward bend 148 is formed so that the ultimate end 150 of side wall 86 near terminal end 88 is substantially parallel, although inwardly displaced, to upper case 80 opposite inward bend 148. The amount of displacement of the terminal end 88 of upper case 80 is about equal to the thickness of the lower case 82.

Figure 10:
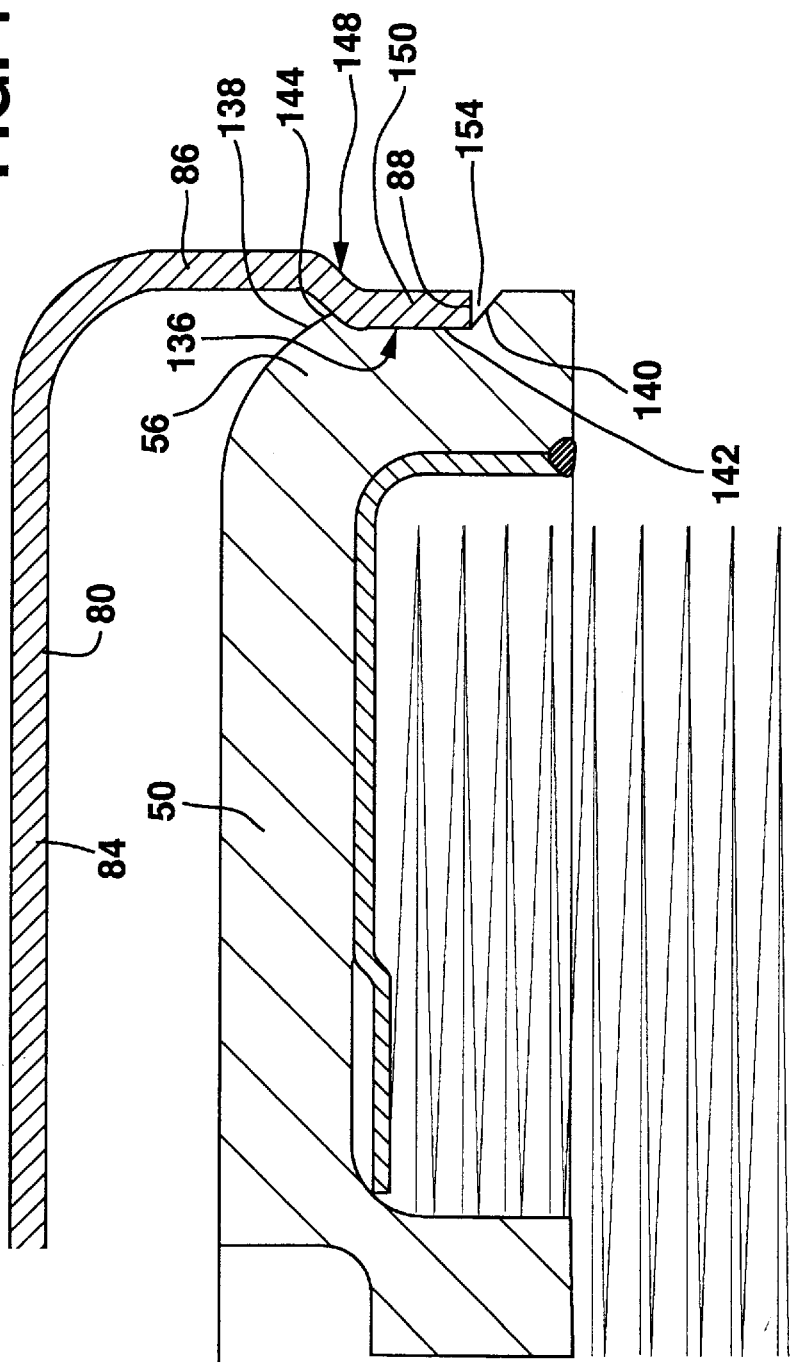
FIG. 10 is a side cross-section view of the placement of the upper case with respect to the bulkhead in one embodiment of the present invention.

To assemble IIP 10, the terminal end 88 of upper case 80 is placed in recess 136 so that the terminal end 88 is located approximately at the recess bottom 140 (FIG. 10). In this position, the inner surface 152 of side wall 86 near the terminal end 88 is in contact with the recess vertical wall 142. In addition, as described above, because recess bottom 140 is obtuse to the recess vertical wall 142, the recess bottom 140 also forms an acute angle with respect to the terminal end 88 of upper case 80. As a result, there is a space 154 between the terminal end 88 and the recess bottom 140.

Figure 11:
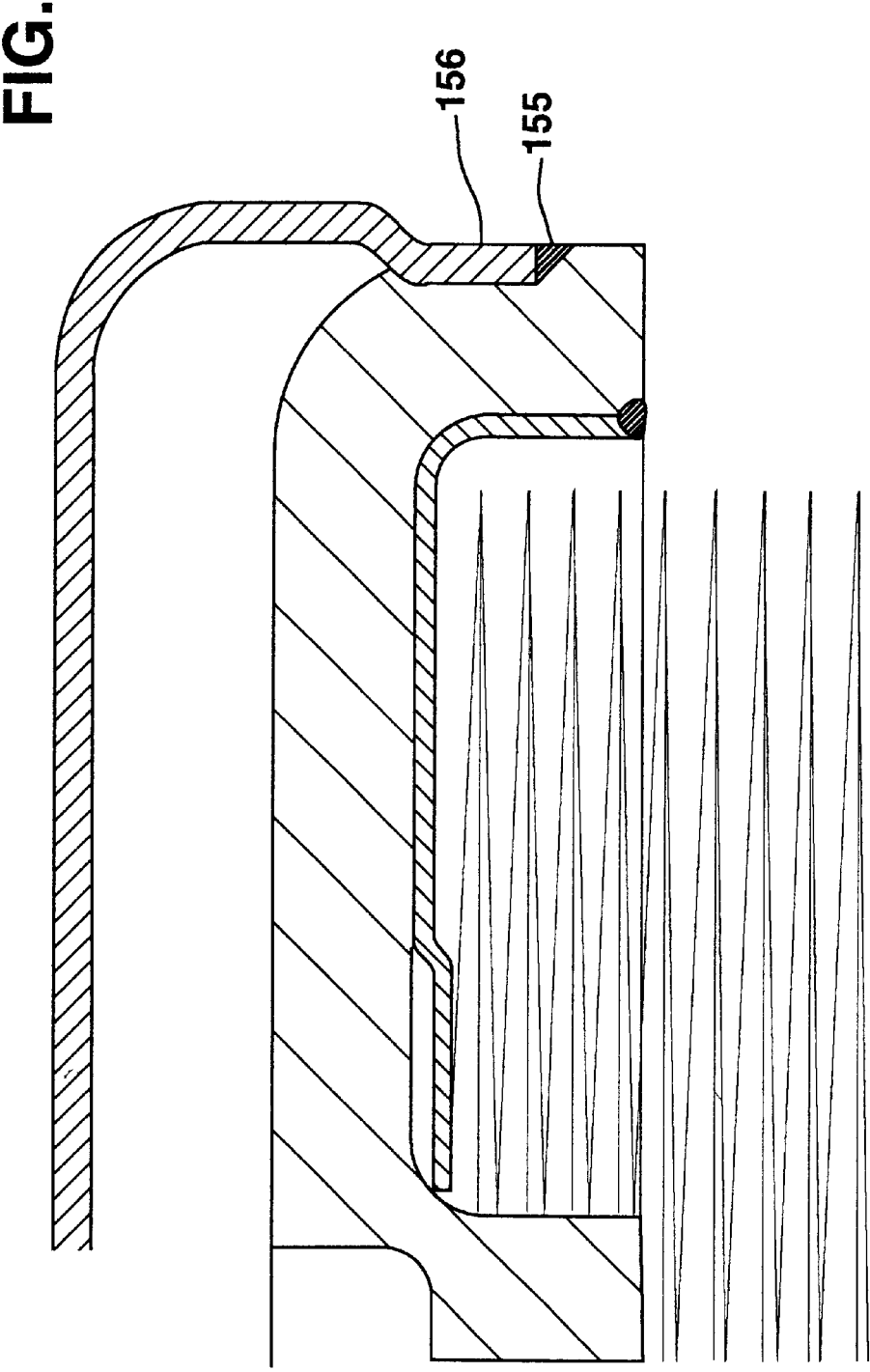
FIG. 11 is a side cross-section view of the connection of the upper case to the bulkhead in the embodiment of FIG. 10.
Figure 12:
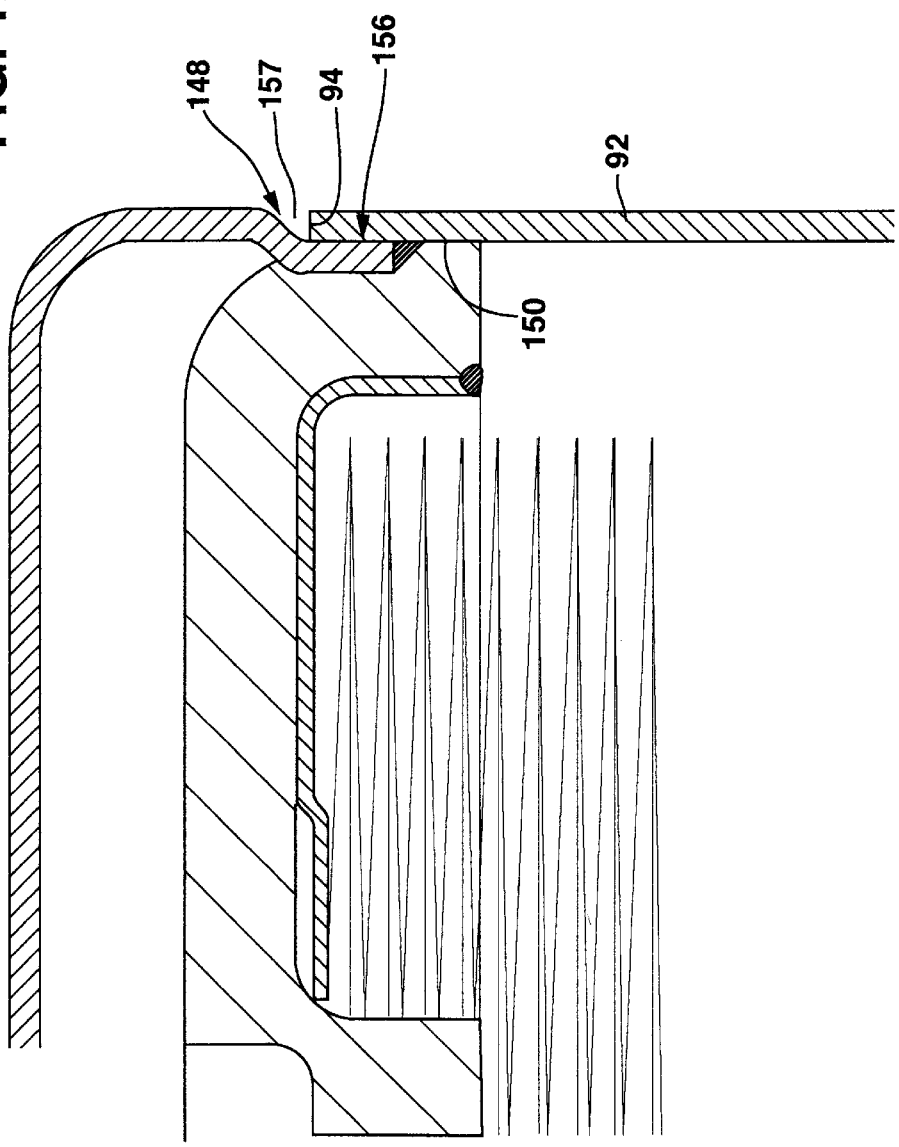
FIG. 12 is a side cross-section view of the placement of the lower case on the upper case in the embodiment of FIG. 10.

As described above, the terminal end 88 of upper case 80 is placed in recess 136 to so that the terminal end 88 is located approximately at the recess bottom 140. Terminal end 88 is attached to bulkhead 50, preferably by welding, so that a weld 155 fills the space 154 between the terminal end 88 and recess bottom 140 (FIG. 11). Preferably, when space 154 is filled with the weld 155 to connect terminal end 88 to bulkhead 50, the weld 155 should be about co-linear with the outer surface 156 of the terminal end 88 of upper case 80. The weld in space 154 forms a seal between bulkhead 50 and the upper case 80.

Figure 13:
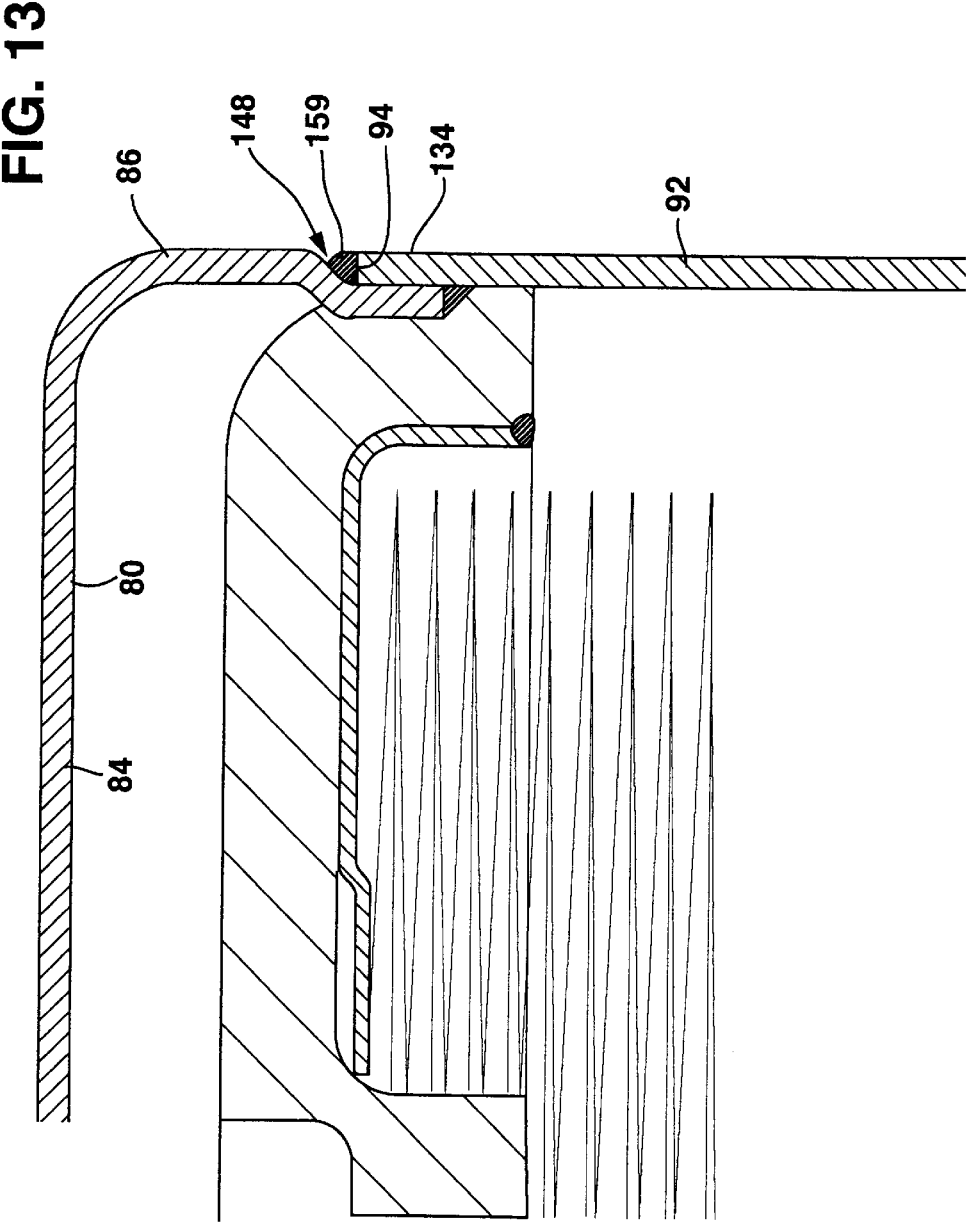
FIG. 13 is a side cross-section view of the connection of the lower case to the upper case in the embodiment of FIG. 10.

After upper case 80 has been attached to bulkhead 50 as described above, the lower case 82 is attached to upper case 80. This is done by moving the terminal end 94 of lower case 82 into contact with the outer surface 156 of the terminal end 88 of upper case 80 so that the inside surface 150 of lower case 82 is in contact with the outer surface 156 of terminal end 88 (FIG. 13). Further, the terminal end 94 is moved to approximately the location of inward bend 148. This produces a space 157 between the terminal end 94 of lower case 82 and the material of upper case 80 near the inward bend 148.

Lower case 82 is attached to upper case 80, preferably by welding lower case 82 to upper case 80 in space 157. Since space 157 extends entirely around the IIP 10, lower case 82 is attached to upper case 80 by a weld 159 in space 157 entirely around the outer periphery of IIP 10 (FIG. 13). Also, the weld 159 in space 157 should attach lower case 82 to upper case 80 and thereby entirely fill space 157 but should not extend above the outer surface 134 of lower case 82 and outer surface 132 of upper case 80. As a result, lower case 82 is attached to upper case 80 through a single seal formed by the weld 159 in space 157 instead of the two seals 104, 106 required by the prior art IIP 10.

The description contained herein is intended to be illustrative of the invention and not an exhaustive description. Many variations and alternatives to the disclosed embodiments will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

We claim:

1. A method of assembling an implantable infusion pump having a reservoir for storing fluid, an outlet port, a metering system for metering fluid in the reservoir to the outlet port, a bulkhead for positioning the reservoir and metering system, the bulkhead having an outer periphery; a first case having a bottom surface and a first case side wall, the first case side wall terminating in a first case terminal end, the first case having a thickness; and a second case having a top surface and an second case side wall, the second case side wall having an inner surface and an outer surface, the second case side wall terminating in an second case terminal end and having an ultimate end near the second case terminal end, the second case having a thickness, the method connecting the second case to the bulkhead and the first case to the second case and comprising the steps of:

forming an inward bend in the second case side wall to form a displaced end portion substantially parallel, although inwardly displaced, to the second case side wall opposite the inward bend, the amount of displacement of the displaced end portion being about equal to the thickness of the first case;

locating and connecting the second case terminal end to the bulkhead whereby the inner surface of the second case side wall near the second case terminal end is in contact with the bulkhead, the step of locating and connecting the second case terminal end to the bulkhead including welding the second case terminal end to the bulkhead; and locating and sealingly connecting the first case terminal end to the outside surface of the displaced end portion whereby the first case is connected to the second case, the step of locating and sealingly connecting the first case terminal end to the outside surface of the displaced end portion including welding the first case terminal end to the second case side wall.

2. The method of claim 1 further comprising forming an annular recess in the outer periphery of the bulkhead extending around the outer periphery; the step of locating and sealingly connecting the second case terminal end to the bulkhead including placing the displaced end portion of the second case in the annular recess.

3. The method of claim 2 in which the step of locating and sealingly connecting the second case terminal end to the bulkhead includes forming a second space adjacent the first case terminal end within the recess, the step of welding the second case terminal end to the bulkhead including placing a second weld within the second space.

4. The method of claim 1 further comprising forming an annular recess in the outer periphery of the bulkhead extending around the outer periphery; the step of locating and sealingly connecting the second case terminal end to the bulkhead including placing the displaced end portion of the second case in the annular recess.

5. The method of claim 4 in which the step of locating and sealingly connecting the second case terminal end to the bulkhead includes forming a second space adjacent the first case terminal end within the recess, the step of welding the second case terminal end to the bulkhead including placing a second weld within the second space.

6. The method of claim 1 in which the reservoir comprises an expandable and contractable bellows structure, the method further comprising sealingly connecting the bellows structure to the bulkhead.

7. The method of claim 6 in which the step of sealingly connecting the bellows structure to the bulkhead comprises welding the bellows structure to the bulkhead.

8. The method of claim 1 in which the step of locating and sealingly connecting the first case terminal end to the outside surface of the displaced end portion includes forming a first space between the second case terminal end and the inward bend, the step of welding the second case terminal end to the bulkhead including placing a first weld within the first space.

9. The method of claim 1 in which the step of locating and sealingly connecting the first case terminal end to the outside surface of the displaced end portion forms a single outer seal.

10. The method of claim 1 in which the first case comprises a lower case, and the second case comprises an upper case.

11. The method of claim 1 in which the first case comprises an upper case and the second case comprises a lower case.

12. A method of assembling an implantable infusion pump having a reservoir for storing fluid, an outlet port, a metering system for metering fluid in the reservoir to the outlet port, a bulkhead for positioning the reservoir and metering system, the bulkhead having an outer periphery with an upper edge, a lower case having a bottom surface and a lower case side wall, the lower case side wall terminating in a lower case terminal end, the lower case having a thickness and an upper case having a top surface and an upper case side wall, the upper case side wall having an inner surface and an outer surface, the upper case side wall terminating in an upper case terminal end and having an ultimate end near the upper case terminal end, the method connecting the upper case to the bulkhead and the lower case to the upper case and comprising the steps of:

forming an annular recess in the outer periphery extending around the outer periphery at the upper edge at the periphery, the recess having a recess bottom and a vertical wall connecting the recess bottom to the upper edge, the recess bottom having a width about equal to the thickness of the upper case;

forming an inward bend in the upper case side wall so that the ultimate end is substantially parallel, although inwardly displaced, to the upper case side wall opposite the inward bend, the amount of displacement of the upper case terminal end being about equal to the thickness of the lower case, the upper case having a thickness; and locating and connecting the upper case terminal end to the recess bottom whereby the inner surface of the upper case side wall near the upper case terminal end is in contact with the vertical wall, the step of locating and connecting the upper case terminal end to the recess bottom including welding the upper case terminal end to the recess bottom;

locating and connecting the lower case terminal end to the outside surface of the upper case side wall near the inward bend whereby, the lower case is connected to the upper case, the step of locating and connecting the lower case terminal end to the outside surface of the upper case side wall near the inward bend including welding the lower case terminal end to the outside surface of the upper case side wall.

13. An implantable infusion pump comprising;

a reservoir for storing fluid;

an outlet port;

a metering system for metering fluid in the reservoir to the outlet port;

a lower case having an bottom surface and a lower case side wall, the lower case side wall terminating in a lower case terminal end, the lower case having a thickness;

an upper case having a top surface and an upper case side wall, the upper case side wall having an inner surface and an outer surface, the upper case side wall terminating in an upper case terminal end and having an ultimate end near the upper case terminal end, the upper case side wall having an inward bend formed so that the ultimate end is substantially parallel, although inwardly displaced, to the upper case side wall opposite the inward bend, the amount of displacement of the upper case terminal end being about equal to the thickness of the lower case, the upper case having a thickness; and a bulkhead for positioning the reservoir and metering system, the bulkhead having an outer periphery with an upper edge, the outer periphery having an annular recess extending around the outer periphery at the upper edge at the periphery, the recess having a recess bottom and a vertical wall connecting the recess bottom to the upper edge, the recess bottom having a width about equal to the thickness of the upper case;

wherein, the upper case terminal end is located approximately at and connected to the recess bottom whereby the inner surface of the upper case side wall near the upper case terminal end is in contact with the vertical wall;

wherein, the lower case terminal end is located on and connected to the outside surface of the upper case side wall near the inward bend whereby, the lower case is connected to the upper case; and wherein the upper case terminal end is welded to the recess bottom and the lower case terminal end is welded to the outside surface of the upper case side wall.

14. An implantable infusion pump having a reservoir for storing fluid, an outlet port, a metering system for metering fluid in the reservoir to the outlet port, a bulkhead for positioning the reservoir and metering system, the bulkhead having an outer periphery with an upper edge, a lower case having a bottom surface and a lower case side wall, the lower case side wall terminating in a lower case terminal end, the lower case having a thickness and an upper case having a top surface and an upper case side wall, the upper case side wall having an inner surface and an outer surface, the upper case side wall terminating in an upper case terminal end and having an ultimate end near the upper case terminal end, wherein the improvement comprises:

the outer periphery having an annular recess extending around the outer periphery at the upper edge at the periphery, the recess having a recess bottom and a vertical wall connecting the recess bottom to the upper edge, the recess having a width about equal to the thickness of the upper case;

the upper case side wall having an inward bend formed so that the ultimate end is substantially parallel, although inwardly displaced, to the upper case side wall opposite the inward bend, the amount of displacement of the upper case terminal end being about equal to the thickness of the lower case, the upper case having a thickness; and wherein, the upper case terminal end is located approximately at and connected to the recess bottom whereby the inner surface of the upper case side wall near the upper case terminal end is in contact with the vertical wall;

wherein, the lower case terminal end is located on and connected to the outside surface of the upper case side wall near the inward bend whereby, the lower case is connected to the upper case; and wherein the upper case terminal end is welded to the recess bottom and the lower case terminal end is welded to the outside surface of the upper case side wall.

* * * * *